United States Patent [19]

Young

[11] 4,287,184

[45] Sep. 1, 1981

[54] PROCESS FOR HEALING WOUNDS

[75] Inventor: David M. Young, Sherborn, Mass.

[73] Assignee: The Massachusetts General Hospital, Boston, Mass.

[21] Appl. No.: 76,998

[22] Filed: Sep. 19, 1979

Related U.S. Application Data

[63] Continuation-in-part of Ser. No. 854,194, Nov. 23, 1977, Pat. No. 4,185,095.

[51] Int. Cl.$^3$ ..................... A61K 35/37; A61K 37/00
[52] U.S. Cl. ..................................... 424/177; 424/95; 260/112 R
[58] Field of Search .............. 424/95, 177; 260/112 R

[56] References Cited

PUBLICATIONS

Varon, et al.; Biochemistry, 6, No. 7, 1967, pp. 2202–2209.
Young, et al.; Biochemistry, 17, No. 8, 1978, pp. 1490–1498.
Greene, et al.; Biochemistry, 8, No. 9, 1969, pp. 3735–3741.
Smith, et al.; Biochemistry, 8, No. 12, 1969, pp. 4918–4926.
Baker, Jour. of Biological Chem., 250, No. 5, 1975, pp. 1714–1717.
Pantazis, et al., Biochemistry, 16, 1977, pp. 1525–1530.
Konovalov, et al., Tsitologiya, 16, No. 10, 1974, pp. 1268–1274 (full translation submitted in Ser. No. 854,144 considered).

*Primary Examiner*—Joseph Paul Brust
*Attorney, Agent, or Firm*—Paul J. Cook; Marvin C. Guthrie

[57] ABSTRACT

Healing of a wound is accelerated by administering a new form of nerve growth factor having a molecular weight of about 116,000 and which is stable in dilute aqueous solutions. The nerve growth factor is obtained from mouse submandibular gland or mouse saliva. An extract of mouse submandibular gland or mouse saliva is subjected to ion-exchange chromatography to recover a component of the gland or saliva rich in the nerve growth factor and containing proteinaceous material which does not degrade the nerve growth factor. The pure nerve growth factor is obtained by subjecting the component rich in nerve growth factor to at least one additional chromatography step, usually two to four, to recover pure nerve growth factor having a molecular weight of about 116,000. The nerve growth factor is applied directly to the wound.

4 Claims, 8 Drawing Figures

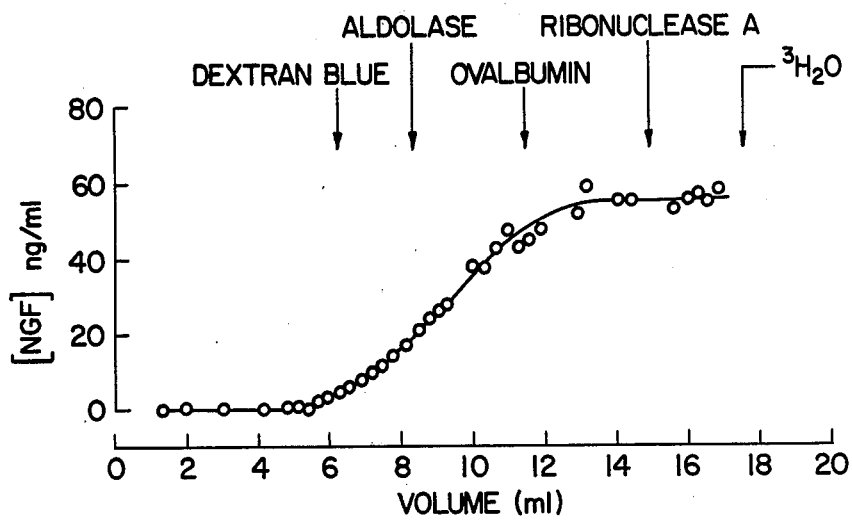
Fig. 7
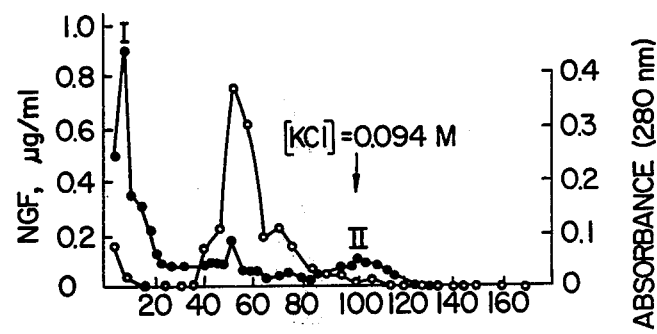
Fig. 8A
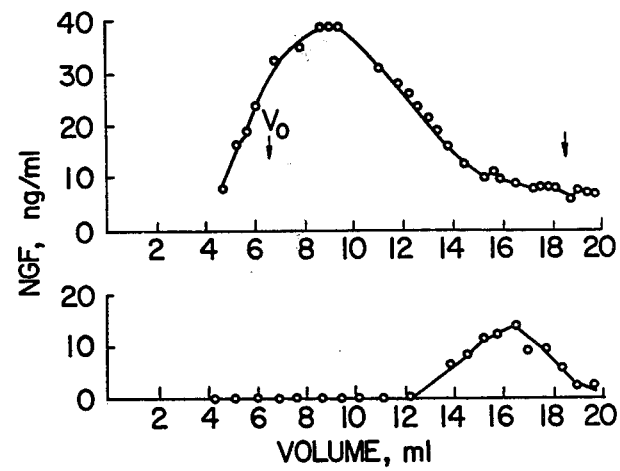
Fig. 8B
Fig. 8C

PROCESS FOR HEALING WOUNDS

The invention described herein was made in the course of work under a grant or award from the Department of Health, Education and Welfare.

REFERENCE TO RELATED APPLICATION

This application is a continuation-in-part application to Ser. No. 854,194, filed Nov. 23, 1977 now U.S. Pat. No. 4,185,095, issued Jan. 22, 1980.

BACKGROUND OF THE INVENTION

This invention relates to a process for utilizing a stable form of nerve growth factor (NGF) for healing wounds.

At the present time, three different molecular forms of NGF have been recognized. Two of these have been isolated from male mouse submandibular glands and have been studied extensively. A third type of NGF is that secreted by mouse L cells in culture. One submandibular gland form has been called 2.5S NGF. This species is a dimer (molecular weight 26,000) composed of two noncovalently linked, identical polypeptide chains whose primary structures are known. In dilute solution, the dimer dissociates into its monomeric subunits (molecular weight 13,000), which are the biologically active species in stimulating ganglionic neurite outgrowth in vitro. The other submandibular gland form has been named 7S NGF. This protein is isolated and purified from submandibular glands by a different procedure from that used to obtain 2.5S NGF. It has a molecular weight of about 140,000 and is composed of three different proteins termed $\alpha$, $\beta$ and $\gamma$. The $\alpha$ and $\gamma$ constituents have no known biological function, although the $\gamma$ species displays arginine esterase activity. Only the $\beta$ component of 7S NGF is biologically active in stimulating neurite outgrowth; by biological and immunological criteria, $\beta$-NGF is indistinguishable from the 2.5S NGF. These two species differ only in that during isolation of either one, limited and different proteolytic modifications occur, the extent of which depends upon the isolation conditions.

The NGF secreted by L cells is yet another species. This protein has a molecular weight close to 160,000 and, like 7S NGF, it contains 2.5S NGF as part of its structure. However, L-cell NGF differs from the 7S complex in at least one important respect. The 7S NGF structure is unstable in solution at neutral pH, and dissociates completely to yield a mixture of its components at concentrations ($\mu$g/ml) nearly 1000 times higher than those required to display biological activity (about 1 ng/ml). Consequently, the biological activity of 7S NFG is due entirely to its 2.5S ($\beta$) component. In contrast to the marked instability of 7S NGF, L-cell NGF is completely stable in very dilute solution and does not dissociate even at concentrations as low as 1 ng/ml. This appreciable difference in stability between gland and L-cell NGF is surprising, since both proteins are of mouse origin. Yet the mouse submandibular gland is rich in proteases, and it seems possible that proteolysis occurring during the process of purification of 7S NGF could account for the instability of the protein.

Prior to the present invention, the known forms of NGF have had no known biological activity other than the stimulation of ganglionic neurite outgrowth.

SUMMARY OF THE INVENTION

This invention utilizes a hitherto unknown form of NGF which is stable including being highly stable in dilute aqueous solutions to heal wounds. It is isolated by a chromatographic procedure and can be isolated in its pure form or in admixture with a protein composition which is inert with respect to its stability characteristics. Fresh extracts of mouse submandibular glands or of mouse saliva are dissolved in an ionic aqueous solution and are subjected to ion exchange chromatography in a first separation step. The NGF-rich fraction obtained contains stable NGF having a molecular weight of about 116,000 and inert proteinaceous material which does not degrade the NGF. Pure stable NGF having a molecular weight of about 116,000 is obtained by subjecting the NGF-rich composition to a plurality of chromatographic separations. The stable NGF-rich fraction or the pure stable NGF is administered to wounds in order to accelerate wound healing.

DETAILED DESCRIPTION OF SPECIFIC EMBODIMENTS

Figure 1:
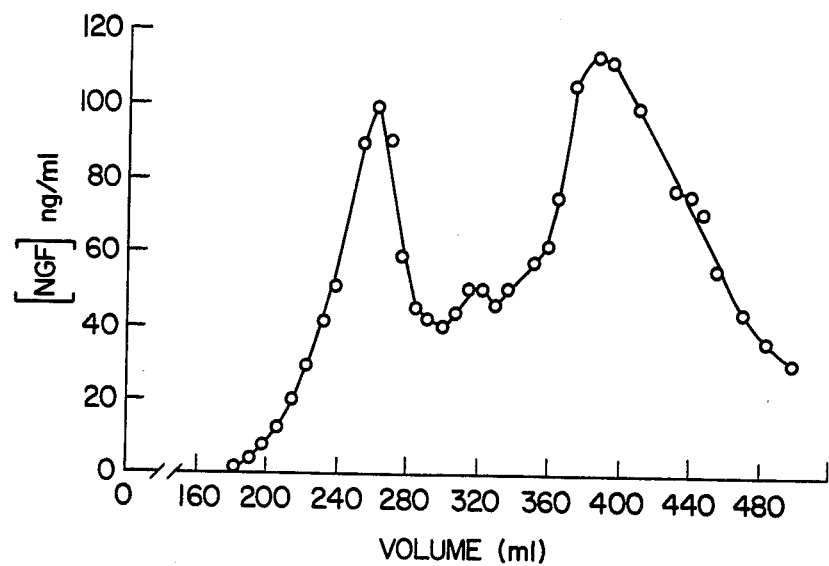

The NGF utilized in this invention is derived from mouse saliva or mouse submandibular glands. It differs from previously recovered NGF in that it is stable even in dilute aqueous solutions and has a molecular weight of about 116,000. The mouse saliva or extract from mouse submandibular glands first is diluted in an aqueous salt solution which does not degrade proteinaceous material. Generally, the aqueous solution has a pH of between about 6 and 9, preferably between about 7 and 8 and an ionic strength of between about 0.01 and 0.2 preferably between about 0.05 and 0.1. The glands are excised from the mouse and homogenized in an ionic aqueous solution. The resultant homogenate is separated to remove solid material from the NGF-rich extract. Similarly, a solution of the saliva is formed by dissolving the saliva in the aqueous salt solution. Representative suitable salts that do not degrade proteinaceous compositions are trishydroxymethylaminomethane (Tris) HCl, potassium phosphate, sodium phosphate, physiological saline at neutral pH or the like.

The solution then is passed through a chromatographic column of a positively charged ion-exchange resin which does not degrade protein molecules and which is equilibrated with the salt solution used to dissolve the NGF extract. The extract is separated into its components within the column. The column then is eluted in a conventional manner with an aqueous salt solution to recover the individual fractions. The NGF-rich fraction contains a proteinaceous composition which does not adversely effect the stability of the NGF. That is, the NGF separated within the column is not subjected to enzymic or proteolytic degradation in contrast to the NGF in its natural state in the gland or in the saliva.

In order to minimize the NGF degradation which occurs in the natural state prior to processing the saliva or excised glands preferably are frozen to a temperature about $-50°$ C., such as by utilizing frozen carbon dioxide (dry ice). The glands or saliva can be homogenized in salt solution either when frozen or after thawing. However, it is preferred to initiate processing while the glands or saliva is frozen in order to minimize NGF degradation.

Suitable resin compositions that can be utilized in the ion-exchange chromatography step are those that are positively charged including diethylaminoethyl Sephadex (cross-linked dextan), diethylaminoethyl cellulose or the like.

Since the NGF fraction recovered by ion-exchange chromatography contains an inert proteinaceous material, it must be treated further in order to isolate the NGF. The fraction determined to have activity as NGF and having a molecular weight of about 116,000 is chromatographed in a resin column a plurality of times until it is determined that the non-NGF components have been separated from the NGF. Suitable means for making this determination include conventional protein sedimentation analysis wherein purification is determined when all of the material in the sample being tested sediments from solution at the same rate.

Suitable resin compositions useful in the secondary chromatographic steps include hydroxylapatite, carboxymethyl cellulose, sephadex or the like.

Prior to each secondary chromatographic step, the NGF-rich fraction obtained from the prior chromatographic separation is dialyzed against a salt solution which does not degrade protein to obtain a protein solution having an ionic strength between about 0.01 and 0.3 and the solution is lyophilized in order to concentrate the protein. The dry powder obtained from the lyophilization step is dissolved in a salt solution having an ionic strength between about 0.01 and 0.2 and a pH between about 6 and 9.

The number of sequential secondary chromatographed separations required to isolate the pure NGF depends upon the purity of the initial sample. Generally, at least 2 and up to about 4 secondary separation steps are required to obtain the pure NGF.

The NGF is utilized in accordance with this invention to accelerate wound healing. The NGF, with or without proteinaceous material that does not degrade the nerve growth factor is administered by being applied to the wound, i.e. topically or by injection. Suitable dosages comprise at least about 1 μg per dose up to concentrations where undesirable side effects are observed. The NGF can be administered alone or in a conventional pharmaceutically acceptable vehicle that does not degrade the NGF such as saline, phosphate buffer or water or the like. The wound healing effect of the NGF of this invention is not observed with other forms of NGF, e.g. 2.5S NGF.

The following examples illustrate the present invention and are not intended to limit the same.

EXAMPLE I

This example illustrates the procedure for isolating pure stable NGF having a molecular weight of about 116,000 from mouse submandibular glands. Activity of the NGF fraction and purity measurements were determined by the procedures set forth below. All mice used in this study were adult CD-1 outbred albino animals obtained from the Charles River Breeding Laboratories, Wilmington, Massachusetts.

Radioimmunoassay of NGF 2.5S NGF was purified from male mouse submandibular glands by the method of Oger et al, 1974, Proc. Natl. Acad. Sci. USA, 71, 155. Preparations were shown to be electrophoretically homogeneous as previously described by Oger et al. Preparation of monospecific antibodies to 2.5S NGF (Oger et al, 1974) as well as the details of preparation of $^{125}$I-NGF and the development and validation of the radioimmunoassy have been presented in detail by Murphy et al, 1975, Proc. Natl. Acad. Sci. USA, 72. 1895 and Young et al, 1977, J. Bio. Chem. 251, 459.

Biological Assays

Sensory ganglion bioassays of NGF were performed with 8-day chick embryo dorsal root ganglia as described by Murphy et al, 1975, Proc. Natl. Acad. Sci. USA, 72, 1895.

Gel Electrophoresis

Samples were electrophoresed with 7.5% polyacrylamide gels at neutral pH at 4° C. Both upper and lower reservoir buffers contained 0.05 M sodium phosphate, pH 7.0; protein solutions were dissolved in 0.01 M sodium phosphate, pH 7.0 containing 0.5 M sucrose and a trace of bromphenol blue. Electrophoresis was performed at a constant current of 8 ma/gel.

Sedimentation Studies

Sedimentation velocity and equilibrium measurements were performed with a Beckman Model E ultracentrifuge equipped with regractometric and absorption scanning optics. The optical systems were freshly realigned prior to these experiments by the procedures of Richards and Schachman, 1959, J. Phys. Chem., 63, 1578 and Schachman et al, 1962, Ultracentrifugation in Biochemistry, New York, N.Y., Academic Press, p. 242. The RITC unit of the instrument was calibrated with a National Bureau of Standards thermometer. Weight-average molecular weights were calculated from the equation:

$$M = \frac{2RT}{(1 - \bar{V}_2\rho)\omega^2} \cdot \frac{d \ln c}{d x^2} \quad (1)$$

and values of $d \ln c/dx^2$ were obtained from the least squares regression coefficients of plots of $\ln 5$ $x^2$. In all cases, the high speed meniscus depletion procedure of Yphantis (1964), Biochemistry, 3, 297 was employed with 3 mm columns of protein solution.

The partial specific volume of NGF was measured with the H$_2$O - D$_2$O procedure of Edelstein and Schachman, 1967 and the equation.

$$\bar{V}_2 = \frac{k - R}{\rho_{D_2O} - R\rho_{H_2O}} \quad (2)$$

where $$R = \frac{(d \ln c/dx^2)_{D_2O}}{(d \ln c/dx^2)_{H_2O}} \quad (3)$$

Here $\pi$ D$_2$O and $\pi$ H$_2$O are the solution densities and k is the ratio of the molecular weight of the deuterated protein to that of the protein H$_2$O. Protein solutions in H$_2$O or D$_2$O were dialyzed for forty-eight hours against solvent to insure complete deuterium exchange. The final D$_2$O concentration following dialysis was estimated to be greater than 99.8 mole %. A value of k=1.0145 was calculated from the amino acid composition of NGF (see below) and this number is close to the value k=1.0155 determined for a variety of proteins by direct measurement of deuterium exchange, Hvidt and Nielsen, 1966, Adv. Protein Chem., 21, 287. Samples of protein dissolved in H$_2$O and D$_2$O were centrifuged simultaneously in a 6-place rotor, and a multiplex system (Beckman) was used to isolate the images of the cells. Multiple scanner traces of each cell were taken after twenty-four and forty-eight hours. Densities of $D_2O$ and $H_2O$ solvents were measured with a 10 ml Leach pycnometer in a constant temperature water bath ($\pm 0.01°$). Where required for sedimentation coefficient calculations, solvent viscosities were determined with an Ostwald-type viscometer.

Protein Concentrations

Protein concentrations were measured by absorbence at $\lambda = 280$ nm. The extinction coefficient of the purified high molecular weight NGF was determined by amino analyses (Beckman Model 121 analyzer) of the protein following twenty-four hour hydrolysis with 6 N HCl in sealed, evacuated tubes. A value of 1.92 ml/mg was obtained.

A radioimmunoassay specific for pure 2.5S NGF was used to detect all forms of NGF in submandibular gland extracts which are immunochemically recognizable by antibody to 2.5S NGF. Thus, in what follows, when reference is made to the concentration of NGF as measured by radioimmunoassay, what is meant is the apparent concentration of the protein based upon known concentrations of 2.5S NGF standards. This distinction between actual protein concentration and that measured immunologically is important since it cannot be assumed that larger molecules, which contain 2.5S NGF as part of their structure, react identically with 2.5S NGF antibodies.

First, the state of NGF as it exists in fresh gland extracts is described. Second, methods are presented for complete purification of the stable undissociated form of the protein. Finally, some properties of the unstable dissociation products of NGF which are present in mouse submandibular gland extracts are described.

NGF in Fresh Submandibular Gland Extracts

FIG. 1 presents a gel filtration profile of immunoreactive NGF in a fresh gland extract. For this experiment, two glands from a single adult male mouse were homogenized (ground-glass) in 5 ml of ice cold 0.1 M potassium phosphate, pH 7.0. Insoluble residue was removed by centrifugation at 40,000× g for 15 min. (4°), and 0.1 ml of the supernatant solution was applied to a large column of G-200 Sephadex operating at 4°. NGF was measured by radioimmunoassay and FIG. 1 illustrates at least three distinct immunoreactive components. It should be emphasized that the pattern presented in FIG. 1 does not arise as a result of the use of glands from a single mouse. All individual mice examined, as well as pooled gland extracts obtained from 100 mice, yield profiles similar to that shown in FIG. 1. However, the relative amounts of the three components depicted in FIG. 1 do vary from animal to animal.

Figure 2:
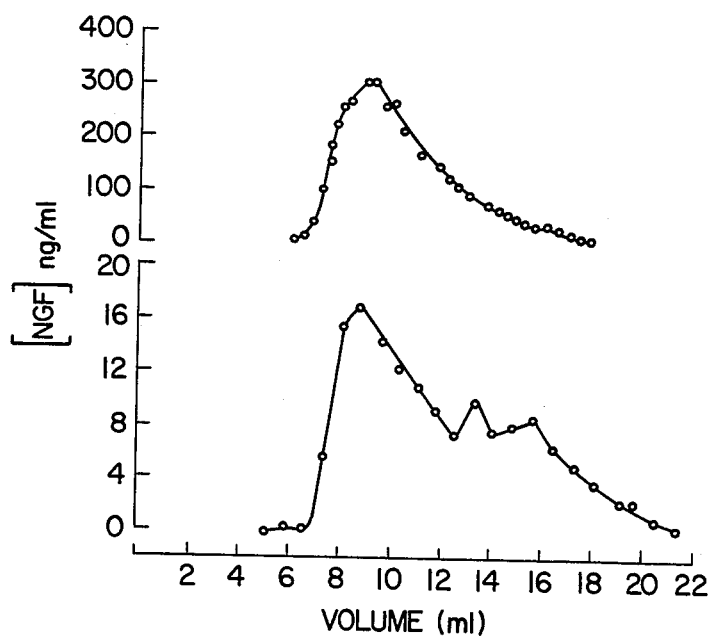

To study the properties of gland extracts as a function both of time following gland removal and of NGF concentration, smaller columns of G-200 Sephadex were employed. FIG. 2 (top) illustrates the gel filtration profile of a fresh gland extract which contained a total of 18 $\mu$g/ml of immunoreactive NGF. In this case, a single peak was observed although it will be seen that it is appreciably asymmetric. However, when the same gland extract used for FIG. 2 (top) was diluted 20-fold to give a concentration of 0.9 $\mu$g/ml NGF, a different gel-filtration pattern was obtained (FIG. 2 (bottom)). The column used for these two experiments was the same, and the gland homogenate remained frozen until chromatographed. As shown in FIG. 2 (bottom), considerable amount of more slowly emerging forms of NGF appear when the gland extract is examined at high dilutions. This behavior indicates the existence of a concentration-dependent dissociation reaction, in which a larger form of NGF is dissociating (initially upon dilution and probably as it migrates down the gel bed) to yield at least two smaller forms. The chromatographic behavior depicted in both FIGS. 1 and 2 is reminiscent of the properties of 7S NGF which also dissociates to yield smaller components as the protein concentration is lowered, Pantazis et al, 1977, Biochemistry, 16, 1525.

To explore the possibility that a time dependent degradation reaction (enzymic or otherwise) was responsible for the results shown in FIGS. 1 and 2, a solution of gland extract identical to that used for the chromatograph shown in FIG. 2 (bottom) was incubated for one hour at 25° and then applied to Sephadex. The resulting profile was virtually identical to that shown in FIG. 2 (bottom). No further dissociation (or degradation) could be detected. The same result was obtained when a whole gland homogenate (without first removing the insoluble residue by centrifugation) was incubated for one hour at 25°. Thus, it appears that the multiple forms of NGF are initially present in gland extracts and that they are not produced by a time-dependent degradation reaction which can be detected in vitro.

Purification and Properties of the Intact Undissociated Form of Gland NGF

Submandibular glands from one hundred adult male mice were excised and frozen with dry ice. After thawing they were homogenized in 55 ml of ice cold 0.025 M tris.HCl, pH 8.0, four 30 second bursts from a Servall Omni-mixer operating at full speed. This mixture was centrifuged for fifteen minutes at 48,000×g, and the supernatant solution was removed and dialyzed with a cellulose membrane for eighteen hours against 4 L of 0.025 M tris.HCl, pH 8.0.

Figure 3:
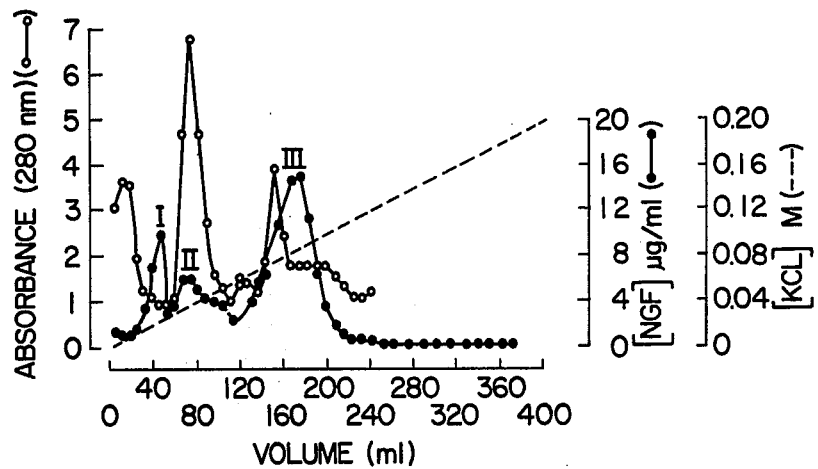

This solution was applied to a 1×23 cm column of DE-52 (microgranular grade), previously packed under a pressure of 8 psi with $N_2$ and equilibrated with 0.025 M tris.HCl, pH 8.0. After the column was loaded, a salt gradient was begun to 0.20 M KCl at a flow rate of 9 ml/hr. Individual fractions were monitored by absorbance and by radioimmunoassay. Under these solvent conditions, 80–90% of the immunoreactive NGF remains bound to the resin prior to initiation of the salt gradient. FIG. 3 illustrates the resulting gradient elution profile, and at least three zones of NGF immunoreactivity can be seen. They are labelled I, II and III for further reference. By area analysis, 75% of the NGF applied to the column was recovered.

Figure 4:
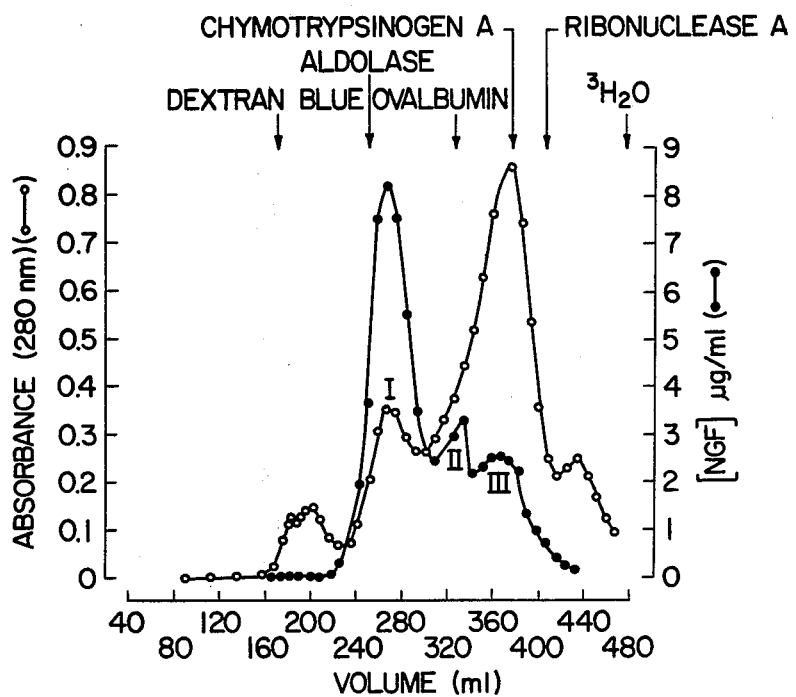

Fractions corresponding to component III were pooled, dialyzed exhaustively against 4 L of 0.001 M potassium phosphate, pH 7.0 and lyophilized. The dry powder was dissolved in 1.0 ml of 0.1 M potassium phosphate, pH 7.0, and applied to a 2.5×95 cm column of G-200 Sephadex equilibrated with the same solvent at 4°. FIG. 4 illustrates the resulting chromatogram and three more peaks containing NGF-immunoreactivity are resolved. As shown in FIG. 4, peak I emerges from the column behind aldolase (molecular weight 158,000), peak II near ovalbumin (molecular weight 45,000), and peak III close to chymotrypsinogen (molecular weight 26,000). The properties of peaks II and III will be considered later. Gel electrophoresis studies at this point revealed that peak I was still considerably inhomogeneous.

Figure 5:
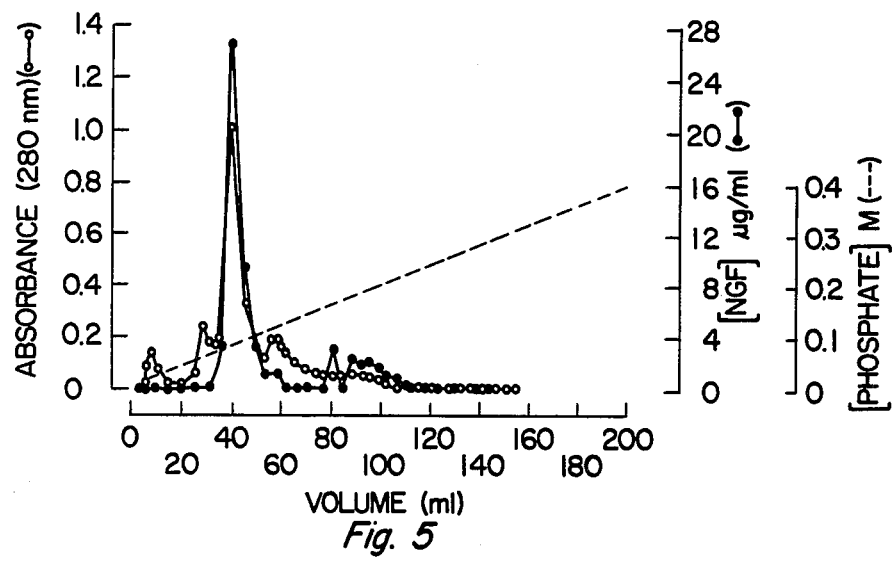

Fractions corresponding to peak I were pooled, dialyzed for eighteen hours against 4 L of 0.001 M potassium phosphate, pH 7.0, and lyophilized. The dry powder was redissolved in 3 ml of 0.01 M potassium phosphate, pH 7.0, and dialyzed thoroughly against this solvent at 4°. This solution was then applied to a 1.3×4 cm column of hydroxylapatite equilibrated with 0.01 M potassium phosphate, pH 7.0, and packed under atmospheric pressure. By radioimmunoassay, quantitative absorption of NGF to the ion exchanger occurs at this stage. A linear gradient from 0.01 M to 0.4 M potassium phosphate, pH 7.0 was begun at 4°, and FIG. 5 illustrates the resulting chromatographic profile. The majority of the NGF immunoreactive material emerges as a single zone coincident with absorbance at a phosphate concentration of 0.074 M. Fractions corresponding to the main NGF zone depicted in FIG. 5 were pooled, dialyzed overnight against 1 L of 0.001 M potassium phosphate, pH 7.0 and lyophilized. The dry powder was redissolved in 2 ml of 0.1 M potassium phosphate, pH 7.0, dialyzed thoroughly against this solvent.

Even at this stage of the procedure, this form of NGF is not completely homogeneous. For example, examination of the preparation by velocity sedimentation revealed a small amount of slowly sedimenting material. To eliminate this component(s), a fourth chromatographic step (using a 2.5×95 cm column of G-200 Sephadex exactly like that used for FIG. 4) is utilized. (The reason for this additional gel filtration step will be apparent when the chromatographic properties of some of the dissociated, lower molecular weight form of NGF are considered.) Fractions from this second G-200 Sephadex column were monitored by absorbance at 280 nm and by radioimmunoassay. Most of the protein emerges at a position identical to that shown in FIG. 4 (peak I), and a small amount of lower molecular weight protein corresponding to peak II (FIG. 4) can be seen and is readily eliminated. The total yield of protein after this final step is about 4 mg.

After pooling and concentrating fractions from the final G-200 Sephadex column, the protein was dissolved in 0.1 M potassium phosphate, pH 7.0 and dialyzed versus this solvent.

A capillary-type synthetic boundary cell was employed for a series of sedimentation velocity profiles of this species, and only a single symmetric sedimenting boundary could be seen. No slower or faster sedimenting material was detected. Table I summarizes values of sedimentation coefficients obtained with both the schlieren and adsorption optical systems. The mean value is $S_{20,w} = 7.37S$. Moreover, when this protein is examined by polyacrylamide gel electrophoresis, only a single sharp band is detected by staining the gel, and all of the NGF-immunoreactive material applied to the gel migrates coincident with this band as judged by radio-immunoassay of serial gel slices.

Figure 6:
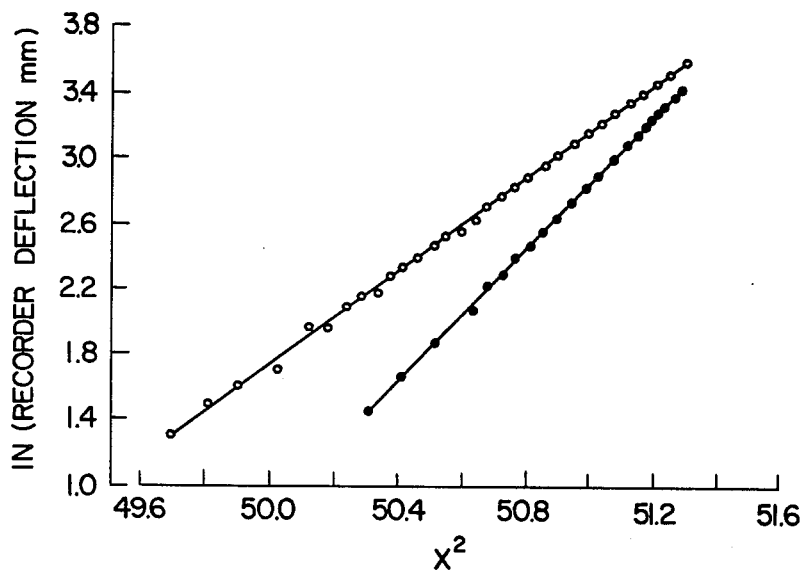

Table II summarizes values of the partial specific volume of the protein determined with $H_2O-D_2O$ procedure. Values of d lnc/dx$^2$ in the two solvents were determined by least squares analyses of multiple scanner traces and representative plots of lnc versus x$^2$ are illustrated in FIG. 6. In both $H_2O$ and $D_2O$, the plots are strictly linnear as would be expected for a pure protein. No curvature of these plots was detected, even at concentrations in the centrifuge cell as low as 40 μg/ml. As shown in Table II, values for $\overline{V}_2$ were measured in two separate experiments and at two different rotor velocities. A mean value of $\overline{V}_2 = 0.688$ ml/g was obtained.

Using the value of $\overline{V}_2$ from Table II, molecular weights were measured at sedimentation equilibrium at three different rotor speeds, in both $H_2O$ and $D_2O$ solvents, and with both absorption and Rayleigh optics. A mean value of 116,000±8,000 (S.D.) was obtained, and the data are presented in Table III.

One of the most interesting features of this 116,000 molecular weight form is its high stability at very low concentrations. As will be shown later, it is the only form of NGF which has been detected in submandibular gland extracts which is stable. FIG. 7 illustrates a typical gel filtration frontal elution profile of a solution of this protein at high dilution. For this chromatogram, a solution of NGF was diluted such that it contained only 50 ng/ml of immunoreactive material, and a large volume of this solution was applied to a 1×23 cm column of G-200 Sephadex equilibrated with 0.1 M potassium phosphate, pH 7.0, in order to establish a plateau region of protein concentration. Gigure 7 reveals only a single symmetric component. The weight average partition coefficient ($\sigma_w$) of this species was calculated from the relation $$\sigma_w = \frac{V_e - V_o}{V_i}$$

where $V_e$, $V_o$ and $V_i$ are the elution volumes of the protein, the void volume and that internal column volume, respectively. Proteins of known molecular weight were used to calibrate the chromatogram depicted in FIG. 7, and from plots of ln (molecular weight) versus $\sigma_w$ for the calibration proteins, a value of 110,000 for the molecular weight of this species of NGF was estimated. This number is in good agreement with that measured (more accurately) by sedimentation equilibrium (Table III). As shown in FIG. 7, the stable NGF purified is stable at protein concentrations as low as 50 ng/ml.

TABLE I

| | Sedimentation Coefficient of NGF[a] | |
|---|---|---|
| Optics | Protein Concentration (mg/L) | $S_{20,w}(S)$ |
| schlieren | 1.0 | 7.50 ± .08 |
| schlieren | 1.7 | 7.56 ± .02 |
| absorption[b] | 0.048 | 7.25 ± .07 |
| | Mean: | 7.37 ± .05 |

[a]Rotor velocity, 60,000 rpm; temperature, 26°; solvent 0.1 M potassium phosphate, pH 7.0. Values for $S_{20,w}$ are given ± the standard deviation of the regression coefficient obtained from plots of ln (radian distance) versus time.
[b]Light of wavelength 230 nm was used with the absorption optical system.

TABLE II

| APPARENT PARTIAL SPECIFIC VOLUME OF NGF[a] | | |
|---|---|---|
| Run | Rotor Speed | $\overline{V}_2$ (ml/g) |
| 1 | 15,000 | 0.69$_0$ |
| 2 | 15,000 | 0.68$_5$ |
| 2 | 17,000 | 0.69$_0$ |
| | Mean: | 0.68$_8$ |

[a]Temperature was maintained close to 26°. The solvents were 0.1 M potassium phosphate, pH 7.0 dissolved in $H_2O$ and in 99.8% $D_2O$. Each value represents the mean calculated from three individual scanner traces (λ = 280 nm) taken after twenty-four hours at the given speed. In run 2, the rotor speed was subsequently increased to 17,000 rpm for an additional twenty-four hours. Protein concentration was 70 μg/ml.

TABLE III

Molecular Weight of NGF[a]

| Run | Rotor Speed | Solvent | Molecular Weight |
| --- | --- | --- | --- |
| 1 | 15,000 | $H_2O$ | 116,000 |
| 1 | 15,000 | $D_2O$ | 123,000 |
| 1 | 17,000 | $H_2O$ | 104,000 |
| 1 | 17,000 | $D_2O$ | 114,000 |
| 2 | 15,000 | $H_2O$ | 120,000 |
| 2 | 15,000 | $D_2O$ | 127,000 |
| 2 | 17,000 | $H_2O$ | 118,000 |
| 2 | 17,000 | $D_2O$ | 125,000 |
| 3 | 15,000 | $H_2O$ | 116,000 |
| 4 | 18,000 | $H_2O$ | 127,000 |
|  |  | Mean: | $116,000 \pm 8,000$ (S. D.) |

[a] Runs 1 and 2 were performed with absorption optics; runs 3 and 4, with Rayleigh optics. The experimental conditions are given in the legend to Table II. Protein concentration, 70 μg/ml. Temperature, 26°; solvent, 0.1 M potassium phosphate, pH 7.0, dissolved either in $H_2O$ or $D_2O$.

The curves shown in the figures were obtained under the conditions set forth below.

FIG. 1. G-200 Sephadex chromatographic profile of NGF in a fresh submandibular gland extract. An extract of a pair of adult male mouse glands was prepared as described in the text. Column dimensions, 95×2.5 cm; solvent, 0.1 M potassium phosphate pH 7.0, containing 1 mg/ml of bovine serum albumin, temperature, 4°. Solution applied (1.0 ml) contained 26.2 μg/ml of NGF as measured by radioimmunoassay. Fractions were measured by radioimmunoassay.

FIG. 2. G-200 Sephadex chromatographic profiles of NGF in a fresh submandibular gland extract as a function of NGF concentration. Column dimensions, 1×23 cm; solvent, 0.1 M potassium phosphate, pH 7.0, containing 1 mg/ml bovine serum albumin; temperature, 4°. Top: 100 μl of 18 μg/ml immunoreactive NGF solution was applied. Bottom: 100 μl of 0.9 μg/ml immunoreactive NGF was applied. Fractions were measured by radioimmunoassay.

FIG. 3. DEAE-cellulose chromatography of a submandibular gland extract. Glands from one hundred adult male mice were homogenized with 55 ml 0.025 M tris.HCl, pH 8.0 as described in the text. Insoluble residue was removed by centrifugation and the supernatant solution was dialyzed against the same solvent at 4°. Column dimensions, 1×23 cm, packed with DE-52 under a nitrogen pressure of 8 p.s.i. and equilibrated at 4° with 0.025 M tris.HCl, pH 8.0. Twenty-six ml of the above solution containing 3.7 mg/ml of immunoreactive NGF was applied to the column. A linear KCl gradient (volume 400 ml) was then begun from 0 to 0.2 KCl at a flow rate of 9 ml/hr. Fractions were measured by absorbance (0—0) (280 nm) and by radioimmunoassay for NGF (●—●).

FIG. 4. G-200 Sephadex chromatography of fraction III from the DE-52 column shown in FIG. 3. Fraction III was desalted, lyophilized and dissolved in 0.1 M potassium phosphate, pH 7.0. This solution was applied to a 2.5×96 cm column of G-200 Sephadex equilibrated with the same solvent at 4°. Flow rate, 26 ml/hr. Fractions were measured for absorbance at 280 nm, (0—0), and by radioimmunoassay for NGF (●—●). The column was subsequently calibrated with the indicated marker proteins, each applied at a concentration of 10 mg/ml, and with dextran blue 2000 and $^3H_2O$.

FIG. 5. Hydroxylapatite chromatography of NGF from peak I shown in FIG. 4. Fractions corresponding to peak I were pooled, desalted and concentrated as described in the text. This solution was dialyzed against 0.01 M potassium phosphate, pH 7.0 and then applied to a 1.3×4 cm column of hydroxylapatite equilibrated with the same solvent at 4°. Following application of the sample (3.9 ml containing a total of 240 μg of immunoreactive NGF), a 200 ml linear gradient of potassium phosphate, pH 7.0, from 0.01 M to 0.4 M was begun. Flow rate, 15 ml/hr. 0—0: absorbance at 280 nm; —— : [NGF], measured by radioimmunoassay.

FIG. 6. Plots of lnc vs $X^2$ for NGF dissolved in $H_2O$ and $D_2O$ at sedimentation equilibrium. NGF was dissolved in and dialyzed against 0.1 M potassium phosphate, pH 7.0, with $H_2O$ and $D_2O$ as solvents as described in the text. Scanner traces (λ=280 nm) were taken twenty-four hours after reaching a speed of 15,000 rpm at 23°. Two double sector cells, one containing protein-$D_2O$ and the other, protein-$H_2O$ solutions were run silmultaneously. Initial protein concentrations was 60 μg/ml. ●—●: $H_2O$; 0—0: $D_2O$.

FIG. 7. Frontal elution G-200 Sephadex profile of NGF at low concentrations. Eighteen ml of 47 mg/ml of immunoractive NGF was applied to a 1×23 cm column equilibrated with 0.1 M potassium phosphate, pH 7.0, containing 1 mg/ml bovine serum albumin at 4°. Flow rates, 6 ml/hr. The calibration proteins (100 μl each at a concentrations of 10 mg/ml) and $^3H_2O$ and blue dextran 2000 were applied separately. Thirty microliter fractions were collected and measured by radioimmunoassay.

EXAMPLE II

This example illustrates that the NGF utilized in this invention can be obtained from mouse saliva.

Saliva was removed from the mice until about 1 ml had been obtained. A column of DE-52 (1×6 cm), equilibrated with 25 mM Tris.HCl, pH 8.0. Saliva (0.3 ml, containing 150 μg/ml of NGF) was diluted with 1.0 ml of 25 mM Tris.HCl, pH 8.0, dialyzed against this solvent, and then applied to the column at 4°. A linear KCl gradient (total volume 200 ml) was begun to 0.2 M KCl at a flow rate of 8 ml/hr. Absorbance was measured at 280 nm. The concentration of NGF was measured by radioimmunoassay. The results are shown in FIG. A. The results in 8B were obtained with a G-200 Sephadex column (1×23 cm). Solvent: 0.1 M potassium phosphate, pH 7.0, containing 1 mg/ml of bovine serum albumin, at 4°. Fractions comprising peak II from the DEAE-cellulose column were pooled, desalted by dialysis, lyophilized and dissolved in 0.5 ml of the column solvent; 200 μl of this solution was applied to the column. Blue dextran and $^3H_2O$ were run separately. The results shown in 8C were obtained under the same conditions as above, except that pooled peak I from the DEAE-cellulose column was chromatographed on Sephadex G-200.

FIG. 8A illustrates the DEAE-cellulose chromatographic profile of saliva; two NGF-immunoreactive components (marked I and II) can be separated. Fractions corresponding to each of these components were pooled separately and then chromatographed upon Sephadex G-200. FIG. 8B reveals that Peak II corresponds to the high-molecular-weight NGF. No lower-molecular-weight NGF was detected. Moreover, the DEAE-cellulose fraction II was completely stable. No dissociation occurred even after 1 week's storage at 4°. FIG. 8C shows that the lower-molecular-weight NGF is completely accounted for in the DEAE-cellulose fraction I. Taken together, the foregoing results indicate that NGF in salvia is unstable, that it is continuously undergoing degradation, and that this process can be prevented by ion-exchange chromatography. Furthermore, it is most likely that the slow transformation of high-molecular-weight NGF in saliva is enzymatically (and probably proteolytically) mediated and that the enzyme responsible is removed by the ion-exchange resin. Any nonenzymatic process, e.g., a slow oxidation reaction, would be expected to continue in spite of ion-exchange chromatography.

The apparent molecular sizes of the two NGF species, both before and after the DEAE-cellulose step, have been estimated by Sephadex G-200 gel filtration, using columns calibrated with proteins of known molecular weights. For this purpose, it is assumed that the gel filtration -ehavior of the two proteins is not anomalous and that they chromatograph like the globular calibration proteins used. Table IV summarizes the weight-average partition coefficients ($\sigma_w$) and corresponding molecular weights. The mean value for the higher-molecular-weight component is 114,000, and for the lighter NGF species, 13,000. The latter number is virtually identical to the molecular weight of the two individual polypeptide chains of $\beta$- and 2.5S (molecular weight 13,259) which have been shown to dissociate from one another at these low protein concentrations. The 13,000-molecular-weight NGF is noncovalently linked to one or more other components to yield the 114,000-molecular-weight species present in saliva.

TABLE IV
PARTITION COEFFICIENTS AND APPARENT MOLECULAR WEIGHTS OF NGF IN SALIVA AND IN SUBMANDIBULAR GLAND HOMOGENATES

| Source* | $\sigma_w$ | Molecular Weight |
|---|---|---|
| Saliva (Sephadex G-200) | 0.21 | 111,000 |
|  | 0.74 | 15,000 |
| Saliva (Sephadex G-200) | 0.20 | 117,000 |
|  | 0.82 | 11,000 |

*Values for molecular weight were estimated from a plot of ln $\sigma_w$ against ln (molecular weight) constructed from values of $\sigma_w$ determined for IgG, serum albumin, and cytochrome c.

EXAMPLE III

This example illustrates that the NGF obtained by the procedures of either Example I or Example II can be utilized to accelerate healing of wounds.

Forty day old Swiss-strain male mice (26–28 g) were obtained from Charles River Breeding Laboratory (Wilmington, Mass.) and each mouse was individually marked and weighted daily throughout the experiment.

A rubber stamp of 1 cm$^2$ stained with India ink was applied to a shaven sacral area on the back of each mouse. Full thickness skin (including the panniculus carnosus muscle) containing the marked area was then excised under ether anesthesia and left to heal by secondary intention. Photography at fixed focal length on alternate days was used to assess the sizes of the wounds. A glass slide with a ruler marked attached was pressed onto each wound so that a flat surface area was presented for photography. Color transparencies of the wounds were projected onto standard graph paper so that 1 cm scale on the slide corresponded to exactly 3 cm on the graph paper. The tracings of the wounds were then cut out and the wound areas represented by the paper weighted. As the thickness of the graph paper is even, the weight of the paper is a good representation of the area.

The animals were then randomly divided into two groups. The first group had the submandibular salivary glands excised through a midline incision, while the other group underwent a sham operation with full mobilization of their submandibular salivary glands. The incisions were closed with 3 0 black silk.

The animals were housed in hanging wire-meshed bottom cages to minimize contamination from their excretions and were fed ad lib with standard laboratory Purina chow. There were between 10to 18 mice in each cage.

In one group all the sham operated animals (n=25) were housed together, while in another group, all the mice with submandibular sialoadenectomy (n=25) were separately kept. In a third group of 18 mice, half were sham operated while the rest had sialoadenectomy, the animals were mixed in the same cage.

The rest of the animals (n=50) had sialoadenectomy and were randomly divided into 5 equal groups of 10 animals, separately caged. One group of 10 animals were given 11 $\mu$g of the NGF having a molecular weight of about 116,000 topically, immediately after wounding and photograph applications were repeated three times with 12 hour intervals. A second group of 10 animals was given the NGF under the scab according to the same time schedule. The other 3 groups of 10 animals were each given respectively equimolar 2.5 S NGF (0.7 $\mu$g), NGF (116,000 MW) inactivated by dinitrofluoro-phosphate (DFP) (7 $\mu$g) or trypsin (0.6 $\mu$g) topically with four applications, immediately and at 3 12-hour intervals. These proteins were administered in a phosphate buffer, pH, 7.0.

The NGF (mw 116,000) utilized in this example was isolated from the submandibular glands of adult male mice and was purified to homogeneity as judged according to the procedure of Example I. Eleven $\mu$g NGF in 100 $\mu$l of 100 mM potassium phosphate pH 7.0 was used on each animal per application, either topically or under the scab.

Di-isopropyl-fluorophosphate (DFP) inhibits the serine protease activity of NGF (116,000 MW) and was therefore used as one of the controls.

A 2.5 S subunit of NGF (mw 26,000) is the moiety that promotes neurite growth in the sensory ganglion assay system and was also used as a control.

Trypsin possessing serine protease activity was also included as another control. The phosphate buffer used as a vehicle for the treating proteins also was used as a control.

The results of this test are shown in Table I.

TABLE I
AVERAGE PERCENT WOUND REMAINING

| Days after operation | 2 | 4 | 6 | 8 | 10 | 12 | 16 |
|---|---|---|---|---|---|---|---|
| Sahm | 62.7 | 58.6 | 37.3 | 23.6 | 16.60 | 11.70 | 5.64 |
| Gland Excised | 88.10 | 82.68 | 70.20 | 41.96 | 24.60 | 15.70 | 11.00 |
| NGF Topical | 68.70 | 62.10 | 55.70 | 36.50 | 24.70 | 13.40 |  |
| NGF Under Wound |  | 59.00 |  | 40.92 |  |  |  |
| Inactivated NGF | 80.40 | 80.50 | 62.20 | 34.60 | 20.00 | 16.10 |  |
| 2.5S NGF | 83.40 | 79.80 | 64.00 | 40.90 | 28.50 | 15.70 |  |
| Trypsin | 84.8 | 78.30 | 66.11 | 48.33 | 25.67 | 16.11 |  |
| Buffer | 78.40 | 72.89 | 58 | 39.38 | 23.63 | 18.25 |  |

As shown in Table I, there is a significant difference in wound size up to 10 days after injury between animals with submandibular salivary glands (sham) and without submandibular salivary glands (gland excised). This is believed to be because the animals having the glands transfer NGF when licking each other's wound. This difference between wound size is abolished after the two groups of animals are mixed in the same cage since the sham animals transfer NGF to the animals without the glands by licking.

The effect of topica-ly applying NGF to animals without submandibular salivary glands is to reduce the size of the wound substantially. As shown in Table I, the average size of the wound after 2 days is about 75% of the wounds of the animals with excised glands. Also as shown in Table I, the effect of the NGF administration appears to dessipate after about 8 days which shows that further NGF administration is needed. The wounds of the animals by NGF injection showed the same healing pattern as the wounds treated with NGF topically The wounds treated with DFP-inactivated NGF, 2.5 S NGF and trypsin, behaved the same as untreated wounds of sialoadenectomized mice, and different significantly from the wounds of the sham-operated animals.

This, the results shown in Table I show that NGF (116,000 MW) significantly improves wound healing.

During this test, no infection was found in any animals. There was more weight loss in the sialoadenectomized animals when compared to the sham controls (12%±1% versus 7%±1%).

I claim:

1. The process for accelerating healing of an animal wound which comprises administering to the wound a nerve growth factor having a molecular weight of about 116,000, said composition being derived from mouse submandibular gland or from mouse saliva which composition is free from the components of mouse saliva or mouse gland which degrade the nerve growth factor in an amount effective to accelerate wound healing, said composition being obtained by dissolving either mouse submandibular or mouse saliva in an aqueous salt solution, and passing said salt solution a plurality of times through a chromatographic column comprising a positively charged ion exchange resin and recovering a fraction of said salt solution rich in a composition having nerve growth factor activity and having a molecular weight of about 116,000.

2. The process of claim 1 wherein said composition contains proteinaceous material derived from mouse saliva or mouse submandibular gland, wherein said proteinaceous material does not degrade the nerve growth factor.

3. The process of claim 1 wherein said composition is substantially free of proteinaceous material derived from mouse saliva or mouse submandibular gland.

4. The process of any one of claims 1, 2 or 3, wherein said composition is admixed with a phamaceutrically acceptable vehicle prior to being administered to said wound.

* * * * *